US012036842B2

(12) United States Patent
Shimomura et al.

(10) Patent No.: US 12,036,842 B2
(45) Date of Patent: Jul. 16, 2024

(54) SLEEPINESS PREDICTION DEVICE, MOVING BODY, AND SLEEPINESS PREDICTION METHOD

(71) Applicant: Panasonic Intellectual Property Management Co., Ltd., Osaka (JP)

(72) Inventors: Yoshihiro Shimomura, Chiba (JP); Yali Xia, Chiba (JP); Shinichi Shikii, Nara (JP)

(73) Assignee: PANASONIC AUTOMOTIVE SYSTEMS CO., LTD., Kanagawa (JP)

( * ) Notice: Subject to any disclaimer, the term of this patent is extended or adjusted under 35 U.S.C. 154(b) by 442 days.

(21) Appl. No.: 17/434,556

(22) PCT Filed: Dec. 17, 2019

(86) PCT No.: PCT/JP2019/049322
§ 371 (c)(1),
(2) Date: Mar. 8, 2022

(87) PCT Pub. No.: WO2020/179186
PCT Pub. Date: Sep. 10, 2020

(65) Prior Publication Data
US 2022/0203804 A1 Jun. 30, 2022

(30) Foreign Application Priority Data
Mar. 1, 2019 (JP) .................................. 2019-037691

(51) Int. Cl.
*B60H 1/00* (2006.01)
*A61B 5/00* (2006.01)
(Continued)

(52) U.S. Cl.
CPC ..... *B60H 1/00742* (2013.01); *A61B 5/14551* (2013.01); *A61B 5/18* (2013.01);
(Continued)

(58) Field of Classification Search
CPC .... B60W 2540/229; B60W 2040/0827; A61B 5/4809; A61B 5/18; A61B 5/14551; B60H 1/008; B60H 1/00742
See application file for complete search history.

(56) References Cited

U.S. PATENT DOCUMENTS

| 2006/0068693 A1* | 3/2006 | Kono ................... B60H 3/0007 454/75 |
| 2016/0179075 A1* | 6/2016 | Shin ....................... G06F 3/016 700/275 |

(Continued)

FOREIGN PATENT DOCUMENTS

| JP | 2001-245871 A | 9/2001 |
| JP | 2002-272708 A | 9/2002 |

(Continued)

OTHER PUBLICATIONS

International Search Report and Written Opinion dated Feb. 10, 2020 in International Patent Application No. PCT/JP2019/049322; with partial English translation.

*Primary Examiner* — Schyler S Sanks
(74) *Attorney, Agent, or Firm* — Rimon P.C.

(57) ABSTRACT

A drowsiness prediction device includes: a carbon dioxide concentration detector that detects the concentration of carbon dioxide in a compartment; an oxygen saturation detector that detects oxygen saturation in the body of a driver present in the compartment; a predictor that predicts, according to the concentration of carbon dioxide and the oxygen saturation detected, a level of drowsiness that the driver would feel after the detection of the concentration of carbon dioxide and the oxygen saturation; and an outputter that outputs information indicating the predicted level of drowsiness.

7 Claims, 5 Drawing Sheets

(51) Int. Cl.
*A61B 5/1455* (2006.01)
*A61B 5/18* (2006.01)
(52) U.S. Cl.
CPC .......... *A61B 5/4806* (2013.01); *A61B 5/7275* (2013.01); *B60H 1/0073* (2019.05); *A61B 2503/22* (2013.01); *A61B 2560/0242* (2013.01)

(56) References Cited

U.S. PATENT DOCUMENTS

2017/0020432 A1* 1/2017 Kusukame ........... A61B 5/0878
2020/0094737 A1   3/2020 Furukawa

FOREIGN PATENT DOCUMENTS

| JP | 2017-117411 A | 6/2017 |
| KR | 10-2010-0053264 A | 5/2010 |
| WO | 2018/190152 A1 | 10/2018 |

* cited by examiner

SLEEPINESS PREDICTION DEVICE, MOVING BODY, AND SLEEPINESS PREDICTION METHOD

CROSS-REFERENCE OF RELATED APPLICATIONS

This application is the U.S. National Phase under 35 U.S.C. § 371 of International Patent Application No. PCT/JP2019/049322, filed on Dec. 17, 2019, which in turn claims the benefit of Japanese Application No. 2019-037691, filed on Mar. 1, 2019, the entire disclosures of which Applications are incorporated by reference herein.

TECHNICAL FIELD

The present disclosure relates to a drowsiness prediction device for predicting drowsiness of a person, a mobile body on which the drowsiness prediction device is provided, and a drowsiness prediction method for predicting drowsiness of a person.

BACKGROUND ART

Conventionally, it is known that in a closed space such as a compartment, an increased concentration of carbon dioxide (in other words, $CO_2$ gas) causes drowsiness, decreased focus and attention, etc., of a person present within the closed space. To deal with this, Patent Literature (PTL) 1 discloses a carbon dioxide concentration notification device that measures the concentration of carbon dioxide in a closed space and outputs ventilation prompting information that suggests the need of ventilation of the closed space, for example.

CITATION LIST

Patent Literature

[PTL 1] Japanese Unexamined Patent Application Publication No. 2017-117411

SUMMARY OF INVENTION

Technical Problem

However, the concentration of carbon dioxide and the drowsiness of a person do not necessarily correlate with each other, and thus the conventional carbon dioxide concentration notification device suggests the need of ventilation of the closed space even when the person does not feel sleepy. In other words, when focusing on drowsiness as a phenomenon, the conventional carbon dioxide concentration notification device is problematic in that its detection accuracy is low.

Thus, an object of the present disclosure is to provide a drowsiness prediction device that predicts the drowsiness of a person with increased accuracy.

Solution to Problem

In order to solve the aforementioned problem, a drowsiness prediction device according to one aspect of the present disclosure includes: a carbon dioxide concentration detector that detects a concentration of carbon dioxide in a compartment; an oxygen saturation detector that detects oxygen saturation in a body of a person present in the compartment; a predictor that predicts, according to the concentration of carbon dioxide detected and the oxygen saturation detected, a level of drowsiness that the person feels after a predetermined time has elapsed since the detection of the concentration of carbon dioxide and the oxygen saturation; and an outputter that outputs information indicating the level of drowsiness predicted.

Advantageous Effects of Invention

According to the present disclosure, a drowsiness prediction device that predicts the drowsiness of a person with increased accuracy is provided.

DESCRIPTION OF EMBODIMENTS

[Outline of Present Disclosure]

In order to solve the aforementioned problem, a drowsiness prediction device according to one aspect of the present disclosure includes: a carbon dioxide concentration detector that detects a concentration of carbon dioxide in a compartment; an oxygen saturation detector that detects oxygen saturation in a body of a person present in the compartment (in other words, a subject); a predictor that predicts, according to the concentration of carbon dioxide detected and the oxygen saturation detected, a level of drowsiness that the person feels after a predetermined time has elapsed since the detection of the concentration of carbon dioxide and the oxygen saturation; and an outputter that outputs information indicating the level of drowsiness predicted.

With this, the concentration of carbon dioxide in the compartment and the oxygen saturation of the subject can be detected. The level of drowsiness of the subject can be predicted according to the detected concentration of carbon dioxide and the detected oxygen saturation of the subject. In addition to the concentration of carbon dioxide, the oxygen saturation that strongly correlates with the drowsiness of the subject can be used. Therefore, when the drowsiness prediction device according to the present disclosure is used, it is possible to predict the drowsiness of the subject with increased accuracy. Furthermore, the drowsiness prediction device according to the present disclosure is capable of predicting the change over time in the drowsiness with each oxygen saturation. Specifically, at the stage at which the concentration of carbon dioxide and the oxygen saturation are detected before the subject feels sleepy, it is possible to predict the subsequent transition of drowsiness of the subject. Thus, before the subject feels sleepy, measures can be taken against drowsiness that may occur in the future.

Furthermore, when the concentration of carbon dioxide is greater than or equal to a threshold value, the predictor may predict the level of drowsiness of the subject to be a first level if the oxygen saturation is a first numerical value, and predict the level of drowsiness of the subject to be a second level indicating drowsiness more severe than drowsiness at the first level if the oxygen saturation is a second numerical value smaller than the first numerical value.

With this, the drowsiness prediction device is capable of indicating which stage the drowsiness of the subject is in, allowing the subject to visually recognize the level of his or her drowsiness with ease.

Furthermore, the drowsiness prediction device may be provided in a mobile body, the compartment may be located in the mobile body, and the subject may be a driver of the mobile body.

With this, inside the compartment of the mobile body which is the closed space, the drowsiness of the driver who operates the mobile body can be predicted with increased accuracy. Furthermore, on the basis of such drowsiness prediction, the driver can take measures against drowsiness that may occur in the future before feeling sleepy. Thus, it is possible to reduce the operations of the mobile body by a driver who is feeling sleepy with impaired ability to make judgments.

Furthermore, the mobile body may include an operation unit exposed to direct touch by the subject driving the mobile body, and the oxygen saturation detector may be attached to the operation unit.

With this, the driver can predict his or her drowsiness with increased accuracy by only operating the mobile body as usual. Thus, even while operating the mobile body as usual, the driver can take measures against drowsiness that may occur in the future before feeling sleepy.

Furthermore, the mobile body may include a ventilator that ventilates the compartment, and the drowsiness prediction device may further include a device controller that controls the ventilator according to the level of drowsiness predicted.

With this, according to the drowsiness of the driver predicted by the drowsiness prediction device, the drowsiness prediction device can further take measures against drowsiness that may occur in the future before the driver feels sleepy. Thus, without making the driver aware, it is possible to reduce the operations of the mobile body by the driver who is feeling sleepy with impaired ability to make judgments.

Furthermore, in a mobile body according to one aspect of the present disclosure, one of the above-described drowsiness prediction devices is provided in the compartment.

With this, inside the compartment of the mobile body which is the closed space, using the drowsiness prediction device provided therein, the drowsiness of the driver can be predicted with increased accuracy. Therefore, the driver can take measures against drowsiness that may occur in the future before feeling sleepy. Thus, it is possible to reduce the operations of the mobile body by the driver who is feeling sleepy with impaired ability to make judgments.

Furthermore, a drowsiness prediction method according to one aspect of the present disclosure includes: obtaining carbon dioxide concentration data indicating a concentration of carbon dioxide in a compartment and oxygen saturation data indicating oxygen saturation in a body of a person present in the compartment, the concentration of carbon dioxide being detected by a carbon dioxide concentration detector, the oxygen saturation being detected by an oxygen saturation detector; predicting, according to the carbon dioxide concentration data obtained and the oxygen saturation data obtained, a level of drowsiness that the subject feels after a predetermined time has elapsed since the detection of the concentration of carbon dioxide and the oxygen saturation; and outputting information indicating the level of drowsiness predicted.

With this, the concentration of carbon dioxide in the compartment and the oxygen saturation of the subject can be detected. The level of drowsiness of the subject can be predicted according to the detected concentration of carbon dioxide and the detected oxygen saturation of the subject. In addition to the concentration of carbon dioxide, the oxygen saturation that strongly correlates with the drowsiness of the subject can be used. Therefore, when the drowsiness prediction device according to the present disclosure is used, it is possible to predict the drowsiness of the subject with increased accuracy. Furthermore, the drowsiness prediction device according to the present disclosure is capable of predicting the change over time in the drowsiness with each oxygen saturation. Specifically, at the stage at which the concentration of carbon dioxide and the oxygen saturation are detected before the subject feels sleepy, it is possible to predict the subsequent transition of drowsiness of the subject. Thus, before the subject feels sleepy, measures can be taken against drowsiness that may occur in the future.

Hereinafter, an embodiment of the present disclosure will be described with reference to the drawings. Note that each embodiment described below shows a general or specific example of the present disclosure. Therefore, the numerical values, structural elements, and the arrangement and connection of the structural elements, steps, the processing order of the steps etc., shown in the following embodiment are mere examples, and are not intended to limit the present disclosure. Thus, among the structural elements in the following embodiment, structural elements not recited in any one of the independent claims which indicate the broadest concepts of the present disclosure will be described as arbitrary structural elements.

Note that the figures are schematic diagrams and are not necessarily precise illustrations. Therefore, scale reduction, etc., in the figures are not necessarily the same. In the figures, substantially identical elements are assigned the same reference signs, and overlapping description is omitted or simplified.

Embodiment

[Drowsiness Prediction Device]
<Configuration>

Figure 1:
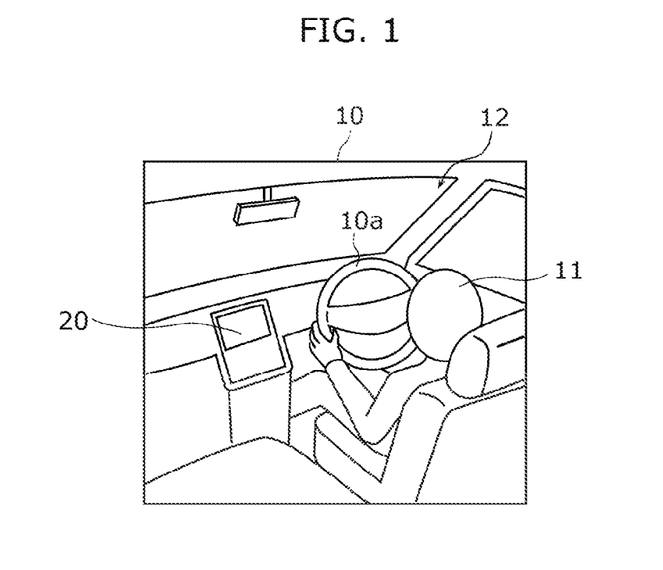
FIG. 1 is a diagram illustrating the use of a drowsiness prediction device according to an embodiment.

First, a drowsiness prediction device according to an embodiment will be described. FIG. 1 is a diagram illustrating the use of the drowsiness prediction device according to the embodiment.

As illustrated in FIG. 1, drowsiness prediction device 20 is provided in compartment 12 of mobile body 10 as one example. In this case, a person (subject) whose drowsiness is to be predicted by drowsiness prediction device 20 is driver 11 who operates mobile body 10 via steering wheel 10*a*. Drowsiness prediction device 20 predicts the level of drowsiness of driver 11 on the basis of the concentration of carbon dioxide in compartment 12 and the oxygen saturation of driver 11. Here, predicting the level of drowsiness means predicting the level of drowsiness that the subject such as driver 11 would feel after a predetermined time has elapsed since the detection of the concentration of carbon dioxide and the oxygen saturation. This means that drowsiness prediction device 20 predicts, on the basis of the current environment around the subject, the effects to be given to the drowsiness of the subject after the predetermined time has elapsed. In other words, drowsiness prediction device 20 predicts the level of drowsiness that the subject would feel after the detection of the concentration of carbon dioxide and the oxygen saturation. Furthermore, drowsiness prediction device 20 performs a predetermined operation according to the level of drowsiness of the subject predicted in this manner.

Figure 2:
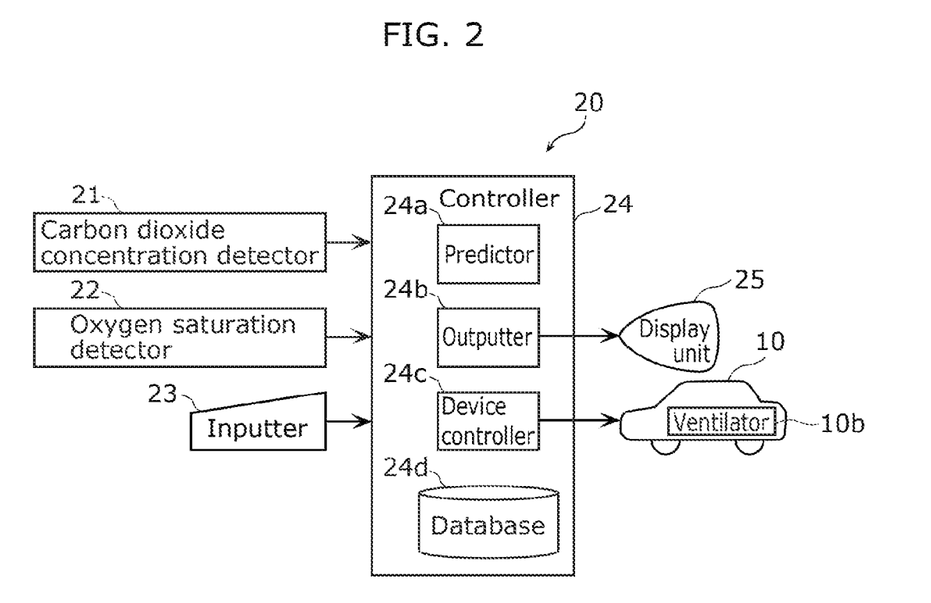
FIG. 2 is a function block diagram of a drowsiness prediction device according to an embodiment.

FIG. 2 is a function block diagram of the drowsiness prediction device according to the embodiment.

As illustrated in FIG. 2, drowsiness prediction device 20 includes carbon dioxide concentration detector 21, oxygen saturation detector 22, inputter 23, and controller 24. Furthermore, display unit 25 and ventilator 10b of mobile body 10 are connected to drowsiness prediction device 20.

Carbon dioxide concentration detector 21 is a gas sensor that detects the concentration of carbon dioxide in compartment 12. For carbon dioxide concentration detector 21, a known gas sensor may be used that is capable of quantitative detection of carbon dioxide in a nondispersive infrared (NDIR) method using infrared light, a semiconductor method using tin oxide, or the like. Carbon dioxide concentration detector 21 is directly or indirectly connected to controller 24 so as to be able to communicate with controller 24. Carbon dioxide concentration detector 21 transmits the detected concentration of carbon dioxide to controller 24.

Oxygen saturation detector 22 is a detection device that detects oxygen saturation in the body of driver 11. More specifically, oxygen saturation detector 22 detects blood oxygen saturation indicating the ratio of oxyhemoglobin to blood hemoglobin in driver 11. Particularly, in the present embodiment, oxygen saturation detector 22 detects arterial blood oxygen saturation ($SpO_2$). Oxygen saturation detector 22 is provided using a reflectance pulse oximeter as one example. The reflectance pulse oximeter includes, for example, an emitter that emits light at two wavelengths of 750 nm and 880 nm and a light receiver that receives a reflected light signal from driver 11. The emitter and the light receiver are configured of a sensor chip in the form of a module. When driver 11 touches the sensor chip, oxygen saturation detector 22 detects the arterial blood oxygen saturation of driver 11. It is sufficient that oxygen saturation detector 22 detect the arterial blood oxygen saturation; a known detection device may be arbitrarily selected. For example, the reflectance pulse oximeter may be replaced by a transmissive pulse oximeter.

Figure 3:
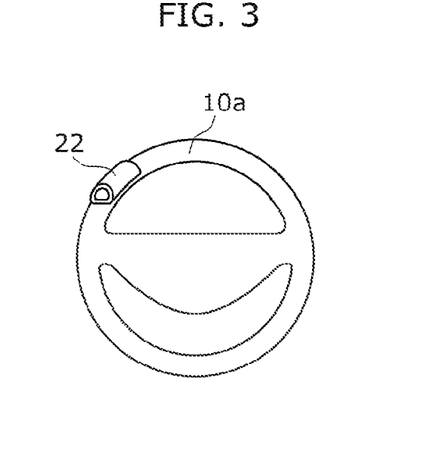
FIG. 3 is a diagram for describing an oxygen saturation detector of a drowsiness prediction device according to an embodiment.

As mentioned earlier, oxygen saturation detector 22 detects the arterial blood oxygen saturation when driver 11 touches the sensor chip. This means that the sensor chip is desirably placed in a position that allows driver 11 to directly touch the sensor chip without difficulties at the time of operating mobile body 10. The position of oxygen saturation detector 22 will be described with reference to FIG. 3. FIG. 3 is a diagram for describing the oxygen saturation detector of the drowsiness prediction device according to the embodiment.

As illustrated in FIG. 3, oxygen saturation detector 22 is provided on steering wheel 10a which is one example of an operation unit to be used to operate mobile body 10, for example. For example, oxygen saturation detector 22 is disposed in an insertion port provided in a gripping portion of steering 10a. The insertion port is sized to allow insertion of a finger of driver 11. This makes oxygen saturation detector 22 visible to driver 11. Thus, it is possible to obtain the arterial blood oxygen saturation by driver 11 inserting his or her finger into the insertion port at any time even while mobile body 10 is in operation.

Note that oxygen saturation detector 22 may be attached to the entire surface of steering wheel 10a so that the arterial blood oxygen saturation of driver 11 can always be detected. The place for oxygen saturation detector 22 is not limited to steering wheel 10a and may be the shift lever (not illustrated in the drawings), the instrument panel, or the like of mobile body 10. Oxygen saturation detector 22 may detect the arterial blood oxygen saturation of driver 11 without contact as long as oxygen saturation detector 22 can emit light to the forehead, etc., of driver 11 and obtain reflected light.

As with carbon dioxide concentration detector 21, oxygen saturation detector 22 is directly or indirectly connected to controller 24 so as to be able to communicate with controller 24. Oxygen saturation detector 22 transmits the detected oxygen saturation to controller 24.

Inputter 23 is a user interface that receives input of driver 11 entered on drowsiness prediction device 20. Inputter 23 is, for example, a touch panel or the like provided in a display of a navigation system or the like embedded in the instrument panel.

As with carbon dioxide concentration detector 21 and oxygen saturation detector 22, inputter 23 is directly or indirectly connected to controller 24 so as to be able to communicate with controller 24. Inputter 23 receives input of driver 11 entered on drowsiness prediction device 20 and transmits the input to controller 24.

Inputter 23 is used by driver 11 to enter various threshold values that are to be set in advance, for example. Although described later, inputter 23 is used when driver 11 determines whether or not to perform some operations of drowsiness prediction device 20 and inputter 23 receives the input of a determination result.

Controller 24 is a processing device that predicts the level of drowsiness of driver 11 on the basis of the concentration of carbon dioxide and the oxygen saturation received from carbon dioxide concentration detector 21 and oxygen saturation detector 22. More specifically, controller 24 includes predictor 24a, outputter 24b, device controller 24c, and database 24d.

Predictor 24a, which is a processor that predicts the level of drowsiness of driver 11 on the basis of the received concentration of carbon dioxide and the received oxygen saturation, is provided using a central processing unit (CPU) and a prediction program stored in a storage capable of performing communication with the CPU, for example. Examples of the storage include read-only memory (ROM), random-access memory (RAM), hard disk drive (HDD), and solid-state drive (SSD).

Predictor 24a is directly or indirectly connected to outputter 24b and device controller 24c so as to be able to communicate with outputter 24b and device controller 24c. In accordance with the prediction program, predictor 24a predicts the level of drowsiness of driver 11 and transmits output information to outputter 24b. Furthermore, in accordance with the prediction program, predictor 24a predicts the level of drowsiness of driver 11 and transmits control information to device controller 24c.

Outputter 24b is directly or indirectly connected to display unit 25 so as to be able to communicate with display unit 25. Display unit 25 is, for example, a display device such as a display and is shared with the display of the navigation system or the like embedded in the instrument panel. Note that display unit 25 may be a simple lamp or the like.

On the basis of the output information received from predictor 24a, outputter 24b transmits (in other words, outputs) image information to be displayed on display unit 25. Display unit 25 displays the image information received from outputter 24b. In other words, outputter 24b is a communication interface connected to display unit 25 to communicate with display unit 25.

Device controller 24c is directly or indirectly connected to ventilator 10b of mobile body 10 so as to be able to communicate with ventilator 10b of mobile body 10. Ventilator 10b is an air-conditioning device or the like included in mobile body 10. Note that ventilator 10b may be a driver that performs an opening/closing control for a window or the like included in mobile body 10.

Device controller 24c transmits operation information for switching the operation of ventilator 10b on the basis of the control information received from predictor 24a. Ventilator 10b switches an operation mode for turning on and off the operation, drawing in outside air, and circulating inside air, for example, on the basis of the received operation information. In other words, device controller 24c is a communication interface connected to ventilator 10b to communicate with ventilator 10b.

Database 24d includes information generated on the basis of the concentration of carbon dioxide and the oxygen saturation to predict the level of drowsiness of driver 11. Specifically, database 24d includes information in which the concentration of carbon dioxide, the oxygen saturation, and the level of drowsiness of the subject that is determined according to the concentration of carbon dioxide and the oxygen saturation are associated with each other. Database 24d is referred to by predictor 24a at the time of predicting the level of drowsiness of driver 11. Predictor 24a may predict, by referring to database 24d as just mentioned, the level of drowsiness that driver 11 would feel after the detection of the concentration of carbon dioxide and the oxygen saturation.

Although details will be described later, predictor 24a may predict the level of drowsiness of driver 11 by an algorithm such as arithmetic processing using the concentration of carbon dioxide and the oxygen saturation detected or may predict the level of drowsiness of driver 11 by referring to database 24d. In the former case, such database 24d is not essential.

<Operations>

Next, the operation of drowsiness prediction device 20 according to the embodiment will be described with reference to FIG. 4.

Figure 4:
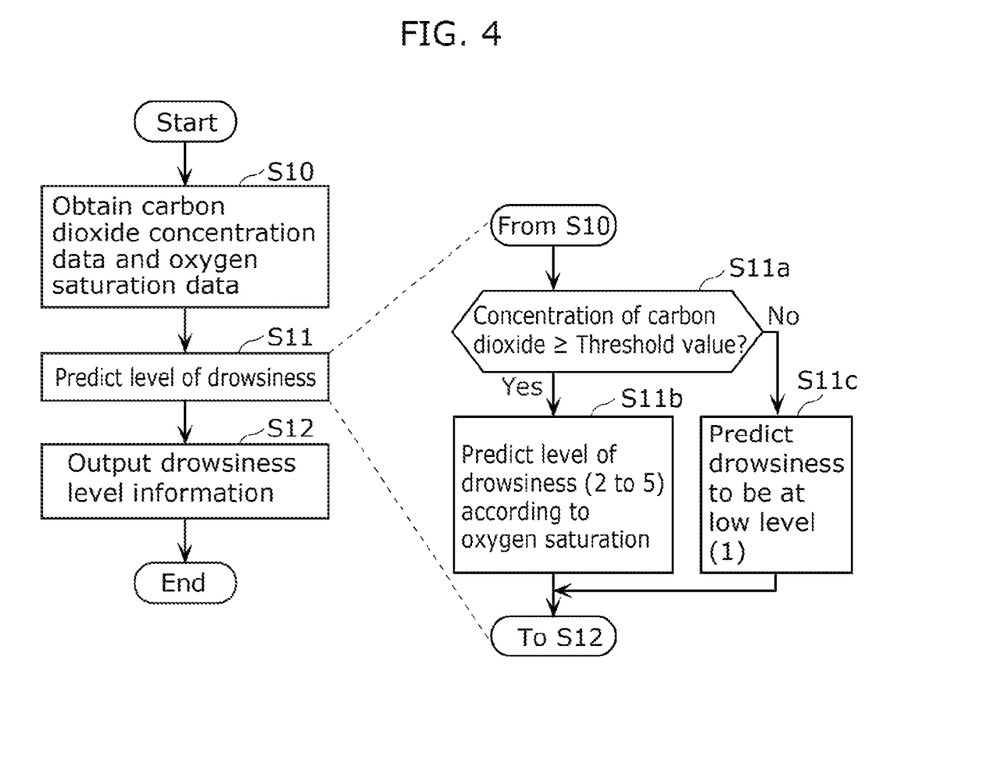
FIG. 4 is a flowchart for describing the flow of drowsiness prediction according to an embodiment.

FIG. 4 is a flowchart for describing the flow of drowsiness prediction according to the embodiment.

First, carbon dioxide concentration detector 21 and oxygen saturation detector 22 detect the concentration of carbon dioxide and the oxygen saturation, respectively. Subsequently, obtainment step S10 is performed in which controller 24 obtains the concentration of carbon dioxide and the oxygen saturation detected. In other words, the concentration of carbon dioxide and the oxygen saturation detected are transmitted to predictor 24a of controller 24. Next, prediction step S11 is performed in which the level of drowsiness of driver 11 is predicted according to the received concentration of carbon dioxide and the received oxygen saturation.

In prediction step S11, first, predictor 24a determines whether or not the received concentration of carbon dioxide is greater than or equal to a threshold value determined in advance (Step S11a). When the concentration of carbon dioxide is less than the threshold value determined in advance (No in Step S11a), predictor 24a predicts the level of drowsiness of driver 11 to be the mildest drowsiness level (Step S11c). In the present embodiment, as one example, the level of drowsiness of driver 11 has five stages from level 1 indicating the mildest drowsiness to level 5 indicating the most severe drowsiness.

Therefore, in Step S11c mentioned above, the drowsiness of driver 11 is indicated as level 1 which is lowest. On the other hand, when the concentration of carbon dioxide is greater than or equal to the threshold value determined in advance (Yes in Step S11a), the level of drowsiness of driver 11 is predicted according to the oxygen saturation (Step S11b).

More specifically, three threshold values of the oxygen saturation, first saturation to third saturation, are set in advance. When the oxygen saturation is higher than or equal to the third saturation which is highest among the three threshold values, the level of drowsiness of driver 11 is predicted to be level 2 indicating drowsiness more severe than the drowsiness in level 1.

Furthermore, when the oxygen saturation has a value greater than or equal to the second saturation which is in the middle among the three threshold values, but less than the third saturation, predictor 24a predicts the level of drowsiness of driver 11 to be level 3 indicating drowsiness more severe than the drowsiness in level 2. Furthermore, when the oxygen saturation has a value greater than or equal to the first saturation which is lowest among the three threshold values, but less than the second saturation, predictor 24a predicts the level of drowsiness of driver 11 to be level 4 indicating drowsiness more severe than the drowsiness in level 3. Furthermore, when the oxygen saturation has a value less than the first saturation, predictor 24a predicts the level of drowsiness of driver 11 to be level 5 indicating drowsiness more severe than the drowsiness in level 4.

In this manner, in prediction step S11, predictor 24a predicts the level of drowsiness of driver 11 on the basis of the preset number of oxygen saturation threshold values that depends on the number of stages. Note that in prediction step S11, this processing may be replaced by predicting the level of drowsiness of the subject by referring to database 24d using the concentration of carbon dioxide and the oxygen saturation detected.

Subsequently, information indicating the predicted level of drowsiness of driver 11 is transmitted to outputter 24b as the output information. Outputter 24b generates image information including the received level of drowsiness of driver 11 and performs output step S12 to transmit (output) the image information to display unit 25 and cause display unit 25 to display the image information.

Figure 5:
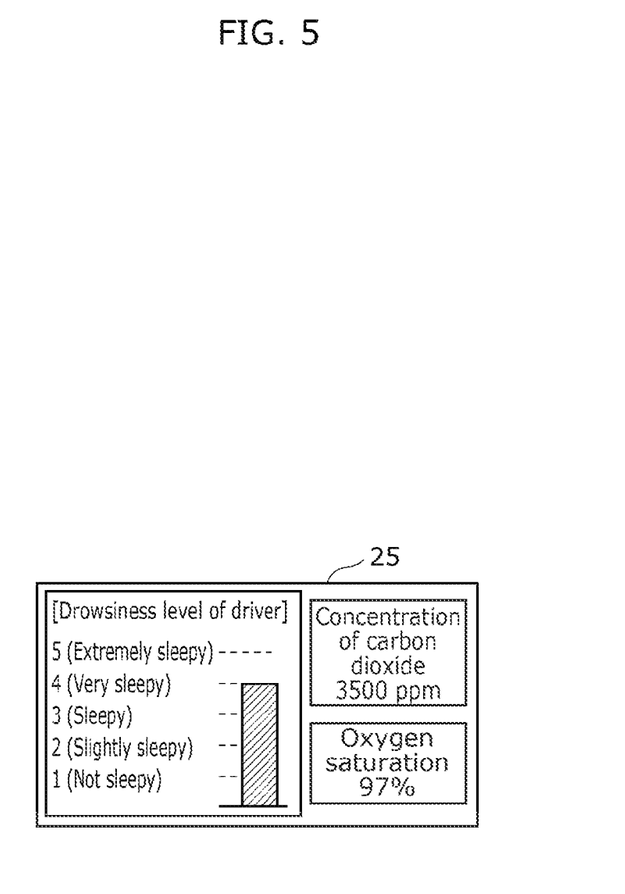
FIG. 5 is a diagram illustrating a screen displayed on a display unit according to an embodiment.

FIG. 5 is a diagram illustrating a screen displayed on the display unit according to the embodiment.

As illustrated in FIG. 5, display unit 25 displays the received image information on the display. The image information includes a scale bar indicating level 1 (Not sleepy), level 2 (Slightly sleepy), level 3 (Sleepy), level 4 (Very sleepy), or level 5 (Extremely sleepy) as the level of drowsiness that driver 11 would feel after a lapse of the predetermined time from the present time. In the figure, as one example, the level of drowsiness that driver 11 would feel after a lapse of the predetermined time from the present time is indicated as level 4. Furthermore, in the image information, the concentration of carbon dioxide currently detected may be displayed in addition. In the figure, as one example, the concentration of carbon dioxide currently detected is indicated as 3,500 ppm. Furthermore, in the image information, the oxygen saturation of driver 11 detected the last time before the present time may be displayed in addition. In the figure, as one example, the concentration of oxygen saturation of driver 11 detected the last time before the present time is indicated as 97%.

Note that the aforementioned configuration of the image information is one example. As another configuration example, only the numerical values of the level of drowsiness, the concentration of carbon dioxide, and the oxygen saturation may be displayed at an end of the image information displayed on display unit 25 by the navigation system. Furthermore, as yet another example, a warning lamp may just light up when the level of drowsiness of driver 11 is greater than or equal to a predetermined level.

Furthermore, in addition to displaying of the image information using display unit 25 mentioned above, when drowsiness prediction device 20 detects the severe drowsiness of driver 11 (for example, at level 4 or 5 as the level of drowsiness), drowsiness prediction device 20 may perform a ventilation step to reduce the concentration of carbon dioxide in compartment 12.

For the level of drowsiness of driver 11 predicted by predictor 24a, a drowsiness level threshold value such as level 4 is set in advance, for example. Predictor 24a determines whether or not the predicted drowsiness level is higher than or equal to the drowsiness level threshold value. When predictor 24a determines that the predicted drowsiness level is higher than or equal to the drowsiness level threshold value, predictor 24a generates the control information and transmits the control information to device controller 24c. On the other hand, when predictor 24a determines that the predicted drowsiness level is lower than the drowsiness level threshold value, predictor 24a realizes only the displaying of the image information using display unit 25 mentioned above.

Device controller 24c transmits operation information for switching the operation of ventilator 10b on the basis of the received control information. More specifically, in the case where ventilator 10b is operating in an inside-air circulation mode, ventilator 10b switches the operation mode into an outside-air draw-in mode on the basis of the operation information. In the case where the operation of ventilator 10b is OFF, the operation of ventilator 10b is set to ON in the outside-air draw-in mode on the basis of the operation information. At this time, by setting the air-conditioning temperature to the current temperature in compartment 12, it is possible to reduce the feeling of strangeness that driver 11 may have.

Note that in the case where ventilator 10b is already operating in the outside-air draw-in mode, an operation may be performed to open a window. Furthermore, such switching of the operation or the like may be automatically performed according to the level of drowsiness of driver 11, or driver 11 may be asked via display unit 25 whether or not to switch the operation, for example. Through the input via input unit 23 of whether or not to switch the operation, driver 11 can switch whether or not drowsiness prediction device 20 transmits the operation information from device controller 24c.

<Relationship Between Oxygen Saturation and Drowsiness>

Figure 6:
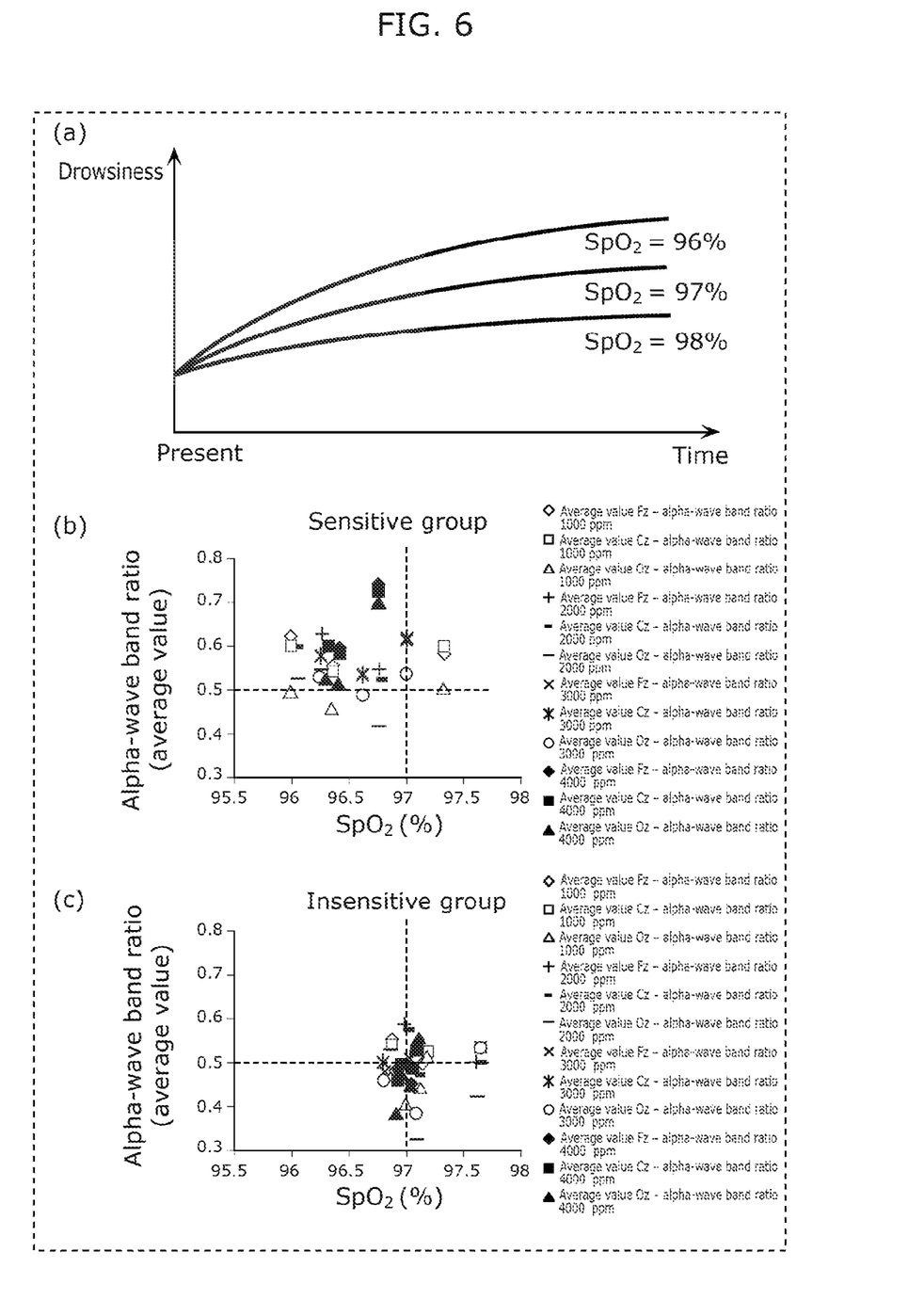
FIG. 6 is a diagram for describing the relationship between oxygen saturation and drowsiness according to an embodiment.

Here, the oxygen saturation and the drowsiness of the subject correlate with each other in such a manner that as the oxygen saturation decreases, the drowsiness of the subject increases. This correlation will be described with reference to FIG. 6. FIG. 6 is a diagram for describing the relationship between the oxygen saturation and the drowsiness according to the embodiment. In FIG. 6, (a) is a graph showing how the drowsiness of the subject changes over time in the cases where the oxygen saturation is 98%, 97%, and 96%.

It is clear from (a) in FIG. 6 that the drowsiness of each subject increases over time. The graph shows that regarding the subject whose oxygen saturation is 98% ($SpO_2$=98%), the drowsiness slightly increases over time starting from the present time. In contrast, regarding the subject whose oxygen saturation is 97% ($SpO_2$=97%), the drowsiness increases at a higher rate than the drowsiness of the subject whose oxygen saturation is 98%. In other words, the graph shows that said drowsiness increases more in a short time. Furthermore, according to the graph, regarding the subject whose oxygen saturation is 96% ($SpO_2$=96%), the drowsiness significantly increases over time starting from the present time and increases at a higher rate than the drowsiness of the subject whose oxygen saturation is 97%.

Thus, as mentioned above, there is a correlation such that as the oxygen saturation decreases, the drowsiness of the subject increases. Furthermore, at the time of predicting the level of drowsiness of the subject, predictor 24a of drowsiness prediction device 20 performs the prediction using such curves.

Generally, it is speculated that as the concentration of carbon dioxide around the subject increases, the drowsiness of the subject increases. However, it is known that regardless of a high concentration of carbon dioxide, the drowsiness of some subjects is more likely to increase while the drowsiness of other subjects is less likely to increase.

In FIG. 6, (b) shows the correlation between the oxygen saturation and the drowsiness of the group of subjects whose drowsiness is more likely to increase (sensitive group). Furthermore, in FIG. 6, (c) shows the correlation between the oxygen saturation and the drowsiness of the group of subjects whose drowsiness is less likely to increase (insensitive group). In each of (b) and (c) in FIG. 6, the horizontal axis represents the oxygen saturation ($SpO_2$), and the vertical axis represents an alpha-wave band ratio. Note that the alpha-wave band ratio is one type of brain waves having a value that increases as the drowsiness increases. Alpha waves are measured at three portions, namely, a frontal portion (Fz), a crown portion (Cz), and an occipital portion (Oz), in the range of the concentration of carbon dioxide between 1,000 ppm and 4,000 ppm, and drowsiness predicted as a result of calculating respective alpha-wave band ratios is shown. Note that each measurement was conducted on more than one subject, and the average value is shown in the figure.

In the insensitive group indicated in (c) in FIG. 6, the oxygen saturation of every subject has a high value (about 97% or more) regardless of the concentration of carbon dioxide. Furthermore, the graph shows that the alpha-wave band ratio of each subject does not change much (that is, a low likelihood of feeling sleepy).

In contrast, in the sensitive group indicated in (b) in FIG. 6, there is a tendency that as the concentration of carbon dioxide increases, the oxygen saturation decreases (approximately 96% to 97%). Furthermore, it was found that the alpha-wave band ratios of relatively many subjects have high values (that is, a high likelihood of feeling sleepy).

These results suggest that by detecting the oxygen saturation during the rise of the concentration of carbon dioxide, it is possible to separate a subject whose drowsiness is more likely to increase and a subject whose drowsiness is less likely to increase regardless of a high concentration of carbon dioxide. In other words, the use of the concentration of carbon dioxide and the oxygen saturation make it possible to more accurately predict the level of drowsiness that the subject would feel after the detection of the concentration of carbon dioxide and the oxygen saturation.

Other Embodiments

Drowsiness prediction device 20 and the drowsiness prediction method according to the present disclosure have been described thus far based on the foregoing embodiment, but the present disclosure is not limited to the foregoing embodiment. For example, forms obtained by various modifications to the exemplary embodiments that can be conceived by those skilled in the art, and forms configured by arbitrarily combining structural elements and functions in the exemplary embodiments without departing from the teachings of the present disclosure are included in the present disclosure.

For example, drowsiness prediction device 20 according to the above embodiment may further predict the current level of drowsiness of the subject. Predicting the current level of drowsiness of the subject means predicting, from various measurement values, the level of drowsiness that the subject is feeling at a point in time when the various measurement values are obtained.

In predicting the current level of drowsiness of the subject, the heart rate and the R-R interval (RRI) may be used as the various measurement values. Furthermore, the heart rate and the RRI may be combined with the concentration of carbon dioxide to predict the level of drowsiness. As an example, the relationship between the heart rate and the concentration of carbon dioxide will be described with reference to FIG. 7.

Figure 7:
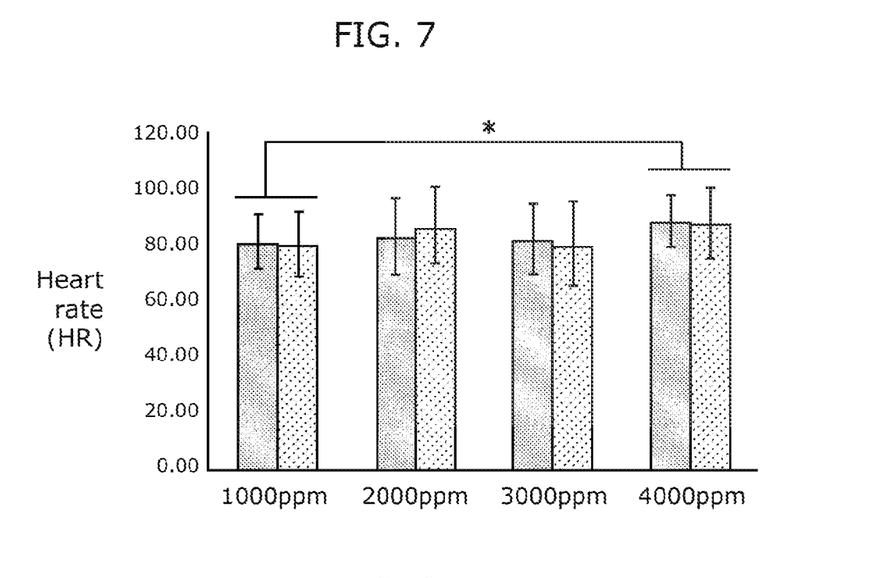
FIG. 7 is a diagram for describing the relationship between the heart rate and the concentration of carbon dioxide.

FIG. 7 is a diagram for describing the relationship between the heart rate and the concentration of carbon dioxide. FIG. 7 shows, by the bar chart, measurement results of the heart rate of a subject who stays in a space with a certain concentration of carbon dioxide for 15 minutes that are measured immediately after the subject enters the space and immediately before a lapse of 15 minutes. The horizontal axis represents each concentration of carbon dioxide between 1,000 ppm and 4,000 ppm. The bar chart shows two bars for each concentration of carbon dioxide, with the left one on the drawing sheet indicating the heart rate immediate after the subject enters the space and the right one on the drawing sheet indicating the heart rate immediate before a lapse of 15 minutes.

FIG. 7 shows that in comparison between the space with a concentration of carbon dioxide of 1,000 ppm and the space with a concentration of carbon dioxide of 4,000 ppm, the heart rate increases significantly (significance level $p<0.05$). In other words, the figure suggests that the heart rate increases with an increase in the concentration of carbon dioxide. Here, it is known that when the concentration of carbon dioxide increases, the subject is likely to feel sleepy. On the other hand, it is known that when the heart rate is high, the subject is less likely to feel sleepy.

For example, when the level of drowsiness of the subject is predicted to be low because the heart rate is increasing, this prediction may be incorrect in the case where the heart rate is increasing simply due to an increase in the concentration of carbon dioxide and the subject is actually likely to feel sleepy by the effects of the concentration of carbon dioxide. Conversely, when the level of drowsiness of the subject is predicted to be high because the heart rate is decreasing, this prediction may be incorrect in the case where the heart rate is decreasing simply due to a decrease in the concentration of carbon dioxide and the subject is actually less likely to feel sleepy without being affected by the effects of the concentration of carbon dioxide.

Thus, at the time of predicting the level of drowsiness of the subject using the heart rate, making correction by using the concentration of carbon dioxide in combination enables more accurate prediction of the level of drowsiness.

Furthermore, there is a suggestion that substantially the same phenomenon occurs in the R-R interval. More specifically, there is a suggestion that the variation in the R-R interval is reduced as the concentration of carbon dioxide increases. As mentioned earlier, when the concentration of carbon dioxide increases, the subject is likely to feel sleepy. Meanwhile, it is known that when the variation in the R-R interval is small, the subject is less likely to feel sleepy.

Thus, at the time of predicting the level of drowsiness of the subject using the R-R interval, making correction by using the concentration of carbon dioxide in combination enables more accurate prediction of the level of drowsiness. Note that the level of drowsiness of the subject may be predicted using both the heart rate and the R-R interval.

Furthermore, for example, drowsiness prediction device 20 does not need to be provided in mobile body 10. For example, drowsiness prediction device 20 may be installed in a space such as an office. Furthermore, at this time, the detected concentration of carbon dioxide may not only be simply displayed on display unit 25, as illustrated in FIG. 5, but also be displayed as a discomfort index indicating the level of discomfort in compartment 12 based on the concentration of carbon dioxide. The discomfort index will be described with reference to FIG. 8.

Figure 8:
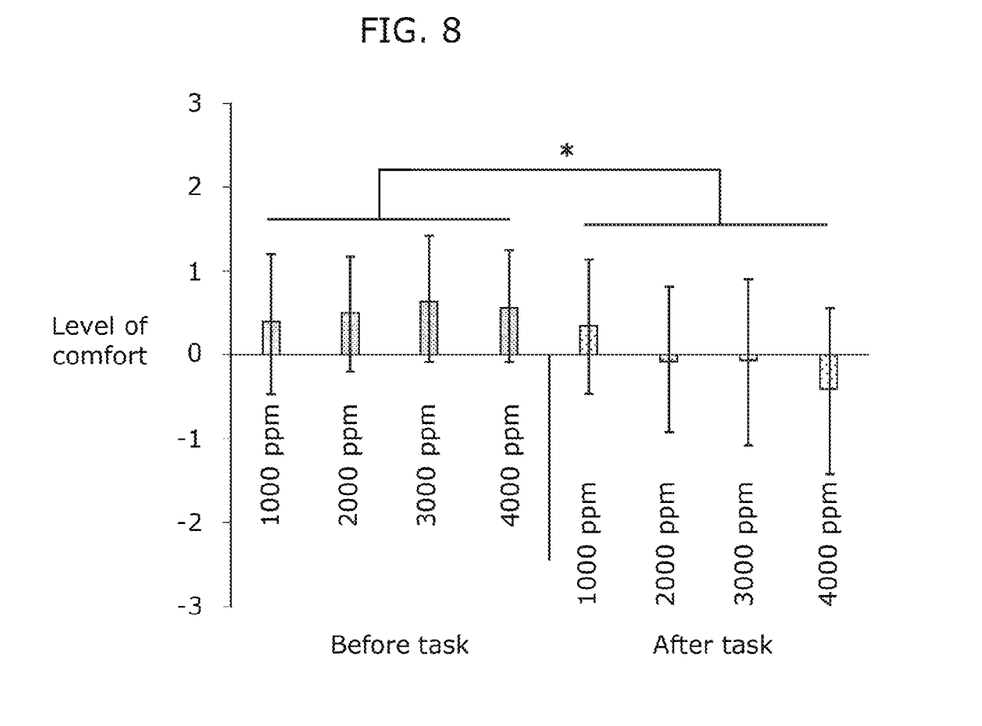
FIG. 8 is a diagram for describing the relationship between the level of discomfort and the concentration of carbon dioxide.

FIG. 8 is a diagram for describing the relationship between the level of discomfort and the concentration of carbon dioxide. In FIG. 8, the horizontal axis represents each concentration of carbon dioxide before and after a task, and the vertical axis represents the level of comfort felt by each subject. The task is a piece of work to be performed by the subject for 15 minutes. Regarding the level of comfort, 0 is set to the criterion, a larger value indicates being more comfortable, and a smaller value indicated being more uncomfortable. In other words, the level of comfort and the level of discomfort are an integral index.

As shown in FIG. 8, when the task is performed in the space with a concentration of carbon dioxide of 1,000 ppm, the level of comfort therein does not change much. On the other hand, when the task is performed in the space with a concentration of carbon dioxide of 4,000 ppm, the level of comfort therein changes from a positive value indicating being comfortable to a negative value indicating being uncomfortable; this space was found to be not suitable for the task.

Therefore, displaying the discomfort index indicating the level of discomfort in compartment 12 based on the concentration of carbon dioxide allows the subject to easily recognize, as an index, operational efficiency dependent on an increase in the concentration of carbon dioxide in compartment 12. The subject can change air in the space, for example, according to the discomfort index, to suppress the predicted drowsiness and make the environment suitable for the task.

Furthermore, for example, the above embodiment describes the configuration in which the level of drowsiness is predicted stepwise using the oxygen saturation, but the level of drowsiness may be predicted using numerical values without stages. Alternatively, a binary configuration may be applied in which a threshold value of the oxygen saturation is set in advance and the drowsiness is determined to increase only when oxygen saturation exceeding said threshold value is detected.

Furthermore, in the configuration according to the above embodiment, the oxygen saturation detected when the concentration of carbon dioxide is greater than the threshold value set in advance is used. As another configuration example, when the oxygen saturation is low, whether or not the low oxygen saturation is based on the drowsiness may be determined using the concentration of carbon dioxide. If the oxygen saturation is low and the concentration of carbon dioxide has not increased, there is a possibility that driver 11 has a health issue, and thus a warning may be output to inform that there is an anomaly different from the level of drowsiness.

Furthermore, for example, the foregoing describes the configuration in which the operation of ventilator 10b is switched using device controller 24c, but drowsiness prediction device 20 may be configured to simply display the image information on display unit 25 to prompt driver 11 to watch for drowsiness.

Furthermore, for example, the present disclosure can be implemented not only as drowsiness prediction device 20, but also as a program including, as steps, processing to be performed by the structural elements of drowsiness prediction device 20 and a computer-readable recording medium having said program recorded thereon. The program may be recorded on the recording medium in advance or may be supplied to the recording medium via a wide-area communication network such as the Internet.

In other words, the above-described general and specific aspects may be implemented using a system, a device, an integrated circuit, a computer program, or a computer-readable recording medium, or any combination of systems, devices, integrated circuits, computer programs, or recording media.

INDUSTRIAL APPLICABILITY

The present disclosure is used for a system or the like that is provided in a movable body or the like and predicts, on the basis of parameters obtained at present, drowsiness that a driver or the like would feel in the future.

The invention claimed is:

1. A drowsiness prediction device, comprising:
a carbon dioxide concentration detector that detects a concentration of carbon dioxide in a compartment;
an oxygen saturation detector that detects oxygen saturation in a body of a person present in the compartment;
a predictor that predicts, according to the concentration of carbon dioxide detected and the oxygen saturation detected, a level of drowsiness that the person feels after a predetermined time has elapsed since the detection of the concentration of carbon dioxide and the oxygen saturation; and
an outputter that outputs information indicating the level of drowsiness predicted,
wherein when the concentration of carbon dioxide is greater than or equal to a threshold value, the predictor predicts the level of drowsiness of the person to be a first level if the oxygen saturation is a first numerical value, and predicts the level of drowsiness of the person to be a second level if the oxygen saturation is a second numerical value smaller than the first numerical value, the second level indicating drowsiness more severe than drowsiness at the first level.

2. The drowsiness prediction device according to claim 1, wherein
the drowsiness prediction device is provided in a mobile body,
the compartment is located in the mobile body, and
the person is a driver of the mobile body.

3. The drowsiness prediction device according to claim 2, wherein
the mobile body includes an operation unit exposed to direct touch by the person driving the mobile body, and
the oxygen saturation detector is attached to the operation unit.

4. The drowsiness prediction device according to claim 2, wherein
the mobile body includes a ventilator that ventilates the compartment, and
the drowsiness prediction device further comprises a device controller that controls the ventilator according to the level of drowsiness predicted.

5. A mobile body, wherein
the drowsiness prediction device according to claim 2 is provided in the compartment.

6. A drowsiness prediction method, comprising:
obtaining carbon dioxide concentration data indicating a concentration of carbon dioxide in a compartment and oxygen saturation data indicating oxygen saturation in a body of a person present in the compartment, the concentration of carbon dioxide being detected by a carbon dioxide concentration detector, the oxygen saturation being detected by an oxygen saturation detector;
predicting, according to the carbon dioxide concentration data obtained and the oxygen saturation data obtained, a level of drowsiness that the person feels after a predetermined time has elapsed since the detection of the concentration of carbon dioxide and the oxygen saturation; and
outputting information indicating the level of drowsiness predicted,
wherein when the concentration of carbon dioxide is greater than or equal to a threshold value, the level of drowsiness of the person is predicted to be a first level if the oxygen saturation is a first numerical value, and the level of drowsiness of the person is predicted to be a second level if the oxygen saturation is a second numerical value smaller than the first numerical value, the second level indicating drowsiness more severe than drowsiness at the first level.

7. A drowsiness prediction device, comprising:
a carbon dioxide concentration detector that detects a concentration of carbon dioxide in a compartment;
an oxygen saturation detector that detects oxygen saturation in a body of a person present in the compartment;
a predictor that predicts, by referring to a database in which the concentration of carbon dioxide, the oxygen saturation, and a level of drowsiness of the person are associated with each other, a level of drowsiness that the person feels after a predetermined time has elapsed since the detection of the concentration of carbon dioxide and the oxygen saturation; and
an outputter that outputs information indicating the level of drowsiness predicted,
wherein when the concentration of carbon dioxide is greater than or equal to a threshold value, the predictor predicts the level of drowsiness of the person to be a first level if the oxygen saturation is a first numerical value, and predicts the level of drowsiness of the person to be a second level if the oxygen saturation is a second numerical value smaller than the first numerical value, the second level indicating drowsiness more severe than drowsiness at the first level.

\* \* \* \* \*